United States Patent
Dodo et al.

(10) Patent No.: US 8,841,126 B2
(45) Date of Patent: Sep. 23, 2014

(54) METHOD FOR GENE TRANSFER

(75) Inventors: Katsuyuki Dodo, Otsu (JP); Naoki Saito, Otsu (JP); Hideto Chono, Otsu (JP); Junichi Mineno, Otsu (JP)

(73) Assignee: Takara Bio Inc., Shiga (JP)

( * ) Notice: Subject to any disclaimer, the term of this patent is extended or adjusted under 35 U.S.C. 154(b) by 0 days.

(21) Appl. No.: 13/805,373

(22) PCT Filed: Jun. 29, 2011

(86) PCT No.: PCT/JP2011/064945
§ 371 (c)(1),
(2), (4) Date: Dec. 19, 2012

(87) PCT Pub. No.: WO2012/002452
PCT Pub. Date: Jan. 5, 2012

(65) Prior Publication Data
US 2013/0109096 A1    May 2, 2013

(30) Foreign Application Priority Data

Jun. 30, 2010 (JP) ................................ 2010-148860
Nov. 1, 2010 (JP) ................................ 2010-245368

(51) Int. Cl.
*C12N 15/00* (2006.01)
*C12N 15/867* (2006.01)
*C12N 15/86* (2006.01)
*C12N 15/87* (2006.01)
*C12P 21/04* (2006.01)
*C12P 21/06* (2006.01)

(52) U.S. Cl.
CPC ............ *C12N 15/8676* (2013.01); *C12N 15/86* (2013.01); *C12N 2740/16043* (2013.01); *C12N 15/87* (2013.01)
USPC .......... 435/440; 435/455; 435/466; 435/69.1; 435/70.1; 435/70.3

(58) Field of Classification Search
None
See application file for complete search history.

(56) References Cited

U.S. PATENT DOCUMENTS

| | | | |
|---|---|---|---|
| 5,686,278 A | 11/1997 | Williams et al. | |
| 6,287,864 B1 * | 9/2001 | Bagnis et al. | 435/456 |
| 6,472,204 B1 | 10/2002 | Asada et al. | |
| 6,787,359 B1 * | 9/2004 | Ueno et al. | 435/456 |
| 2008/0044903 A1 * | 2/2008 | Ueno et al. | 435/405 |

FOREIGN PATENT DOCUMENTS

| | | |
|---|---|---|
| EP | 0 870 839 | 10/1998 |
| EP | 1 094 114 | 4/2001 |
| WO | 95/26200 | 10/1995 |
| WO | 97/18318 | 5/1997 |
| WO | 00/01836 | 1/2000 |

OTHER PUBLICATIONS

Lamers et al., "Retronectin®-assisted retroviral transduction of primary human T lymphocytes under good manufacturing practice conditions: tissue culture bag critically determines cell yield" 10(4) Cytotherapy 406-410 (2008).*
Donohue et al. "Fibronectin Fragment CH-296 Inhibits Apoptosis and Enhances ex Vivo Gene Transfer by Murine Retrovirus and Human Lentivirus Vectors Independent of Viral Tropism in Nonhuman Primate CD34+ Cells" 3(3) Molecular Therapy 359-367 (2001).*
International Search Report issued Jul. 26, 2011 in International (PCT) Application No. PCT/JP2011/064945.
International Preliminary Report on Patentability and Written Opinion issued Feb. 12, 2013 in International (PCT) Application No. PCT/JP2011/064945.
B. Bajaj et al., "High Efficiencies of Gene Transfer with Immobilized Recombinant Retrovirus: Kinetics and Optimization", Articles, Biotechnol. Prog., vol. 17, 2001, pp. 587-596.
H. Chono et al., "Removal of Inhibitory Substances with Recombinant Fibronectin-CH-296 Plates Enhances the Retroviral Transduction Efficiency of $CD34^+CD38^-$ Bone Marrow Cells", Rapid Communication, J. Biochem., vol. 130, 2001, pp. 331-334.
Extended European Search Report issued Apr. 11, 2014 in corresponding Application No. 11 800 914.1.
Dodo et al., "An Efficient Large-Scale Retroviral Transduction Method Involving Preloading the Vector into a Retronectin-Coated Bag with Low-Temperature Shaking", PLOS ONE, Jan. 2009, vol. 1, No. 1, pp. e86275.
Pollock et al., "High-Efficiency Gene Transfer into Normal and Adenosine Deaminase-Deficient T Lymphocytes Is Mediated by Transduction on Recombinant Fibronectin Fragments", Journal of Virology, Jun. 1998, vol. 72, No. 6, pp. 4882-4892.
Shin et al., "Lentivirus delivery by absorption to tissue engineering scaffolds", Journal of Biomedical Materials Research Part A, Jan. 1, 2009, vol. A, No. 1, pp. 1252-1259.

* cited by examiner

*Primary Examiner* — Celine Qian
*Assistant Examiner* — Nancy J Leith
(74) *Attorney, Agent, or Firm* — Wenderoth, Lind & Ponack, L.L.P.

(57) ABSTRACT

Disclosed is a method for introducing a gene into a target cell using a retrovirus vector, which is simple and highly efficient. Specifically disclosed is a method for introducing a gene into a target cell using a retrovirus vector, which comprises the steps of (a) placing a liquor containing a retrovirus vector having a foreign gene carried thereon into a culture vessel on which a retrovirus-binding substance has been immobilized, and incubating the liquor at a temperature lower than 25° C. for 4 hours or longer, thereby producing a culture vessel having the retrovirus vector bound thereto, and (b) adding a target cell to the culture vessel that has been produced in step (a) and incubating the culture vessel. The gene introduction method is simple and highly efficient, and is useful particularly in the fields of medicine, cell technology, gene technology, embryologic technology and the like.

6 Claims, No Drawings

METHOD FOR GENE TRANSFER

TECHNICAL FIELD

The present invention relates to a method for transferring a foreign gene into a target cell using a retroviral vector.

BACKGROUND ART

Recently, gene therapies for treating severe genetic diseases, cancers and the like have been developed. Most of the gene therapies which have been examined for clinical application to humans heretofore involve gene transfer into cells using recombinant retroviral vectors. The retroviral vector can stably integrate a foreign gene of interest into chromosomal DNA of target cells. Therefore, gene transfer by the retroviral vector is a preferable means of gene transfer particularly for the gene therapy in which long-term gene expression is desired.

It has been reported that the efficiency of gene transfer using a retroviral vector is increased by use of a cell adhesive substance that binds to retroviruses, such as fibronectin or a fibronectin fragment CH-296 [RETRONECTIN® (recombinant human fibronectin fragment] (e.g., Patent Literature 1). Also, it has been reported that the gene transfer efficiency is further increased by a method comprising adding a solution containing a retroviral vector to a vessel coated with RETRONECTIN® recombinant human fibronectin fragment) followed by incubation for a certain period of time to allow only the viral vector to bind onto RETRONECTIN® (recombinant human fibronectin fragment), removing a supernatant containing an inhibitory substances against infection, and then adding target cells (RETRONECTIN® Bound Virus Infection Method: RBV method) (Patent Literature 2, Non-Patent Literature 1).

The binding of the viral vector to RETRONECTIN® (recombinant human fibronectin fragment) in the RBV method can be enhanced by utilizing centrifugal force (centrifugal RBV method). However, the centrifugal RBV method requires a vessel that can bear centrifugal force and an expensive apparatus for a centrifugal operation, and the operation includes multi-steps. In addition, there is also a problem that it is difficult to scale up the processing capacity when gene transfer into a large amount of cells is required.

CITATION LIST

Patent Literature

Patent Literature 1: WO 95/26200
Patent Literature 2: WO 00/01836

Non Patent Literature

Non-Patent Literature 1: J. Biochem., vol. 130, pp 331-334 (2001)

SUMMARY OF INVENTION

Technical Problems

An object of the present invention is to provide a convenient and effective method for transferring a gene into a target cell using a retroviral vector.

Solution to Problems

Specifically, the present invention relates to:

[1] a method of transferring a foreign gene into a target cell using a retroviral vector, the method comprising the following steps (a) and (b):
 (a) placing a liquid containing a retroviral vector carrying a foreign gene in a culture vessel on which a retrovirus-binding substance is immobilized, followed by incubation at a temperature of less than 25° C. for 4 hours or more to obtain the culture vessel to which the retroviral vector is bound; and
 (b) adding a target cell into the culture vessel obtained by the step (a), followed by incubation;
[2] the method according to item [1], wherein the incubation time in the step (a) is more than 5 hours and not more than 48 hours;
[3] the method according to item [1], wherein the incubation in the step (a) is incubation with shaking;
[4] the method for transferring a gene according to item [1], which comprises the following steps (a) to (b2):
 (a) placing a liquid containing a retroviral vector carrying a foreign gene into a culture vessel on which a retrovirus-binding substance is immobilized, followed by incubation at a temperature of less than 25° C. for 4 hours or more to obtain the culture vessel to which the retroviral vector is bound;
 (b1) washing the culture vessel obtained by the step (a); and
 (b2) adding a target cell into the culture vessel washed in the step (b1), followed by incubation;
[5] the method according to item [1], wherein the retrovirus-binding substance is at least one selected from the group consisting of fibronectin, fibroblast growth factor, collagen type V, polylysine and DEAE-dextran, as well as fragments thereof;
[6] the method according to item [1], wherein the retrovirus-binding substance also has a cell-binding activity;
[7] the method according to item [1], wherein the culture vessel on which a retrovirus-binding substance is immobilized is a culture vessel on which a retrovirus-binding substance and a cell-binding substance are immobilized; and
[8] the method according to item [7], wherein the cell-binding substance having is at least one selected from the group consisting of cell-adhesive proteins, hormones, cytokines, antibodies, sugar chains, carbohydrates, and metabolites.

Advantageous Effects of Invention

According to the present invention, a convenient and effective gene transfer method is provided.

MODE FOR CARRYING OUT THE INVENTION

The gene transfer method of the present invention comprises a step (a) of "placing a liquid containing a retroviral vector carrying a foreign gene in a culture vessel on which a retrovirus-binding substance is immobilized, followed by incubation at a temperature of less than 25° C. for 4 hours or more to obtain the culture vessel to which the retroviral vector is bound" and a step (b) of "adding a target cell into the culture vessel obtained by the step (a), followed by incubation".

The retrovirus as used herein collectively means RNA viruses belonging to Retroviridae whose genome is composed of RNA and which have a life cycle of converting the RNA to DNA in infected cells, and includes oncoretroviruses and lentiviruses. Examples of the oncoretrovirus include Moloney murine leukemia virus (MMLV). Examples of the lentivirus include human immunodeficiency virus 1 (HIV-1) and simian immunodeficiency virus (SIV).

The retroviral vector as used herein refers to virus particles produced on the basis of retroviruses such as oncoretroviruses, or lentiviruses by recombinant DNA technology, and includes oncoretroviral vectors, lentiviral vectors, and pseudotyped vectors thereof. Examples of the oncoretroviral vector include MMLV-based vectors. Examples of the lentiviral vector include HIV-1-based vectors and SIV-based vectors. The pseudotyped vector refers to a recombinant retroviral vector having an Env protein derived from a virus different from the origin of Gag and Pol proteins. Examples of the pseudotyped vector include oncoretroviral and lentiviral vectors having Env proteins derived from vesicular stomatitis virus (VSV), gibbon ape leukemia virus (GaLV), feline endogenous virus RD114, murine leukemia virus (Ecotropic-env, amphotropic-env, 10A1-env, etc.) and the like. In the present invention, a replication-deficient recombinant retroviral vector is preferably used. The replication ability of the replication-deficient recombinant retroviral vector is eliminated so that the vector cannot autonomously replicate in infected cells, and therefore the vector is non-pathogenic. The vector can infect a host cell such as a vertebrate cell, particularly a mammalian cell, and stably integrate a foreign gene carried by the vector into the chromosomal DNA of the host cell.

The liquid containing a retroviral vector used in the step (a) of "placing a liquid containing a retroviral vector carrying a foreign gene in a culture vessel on which a retrovirus-binding substance is immobilized, followed by incubation at a temperature of less than 25° C. for 4 hours or more to obtain the culture vessel to which the retroviral vector is bound" is not particularly limited, and examples thereof include a culture supernatant of virus-producing cells containing a retroviral vector. In the step (a), after placing a liquid containing a retroviral vector carrying a foreign gene in a culture vessel on which a retrovirus-binding substance is immobilized, the culture vessel containing the liquid may be frozen and stored for a certain period. In this case, the culture vessel with the liquid containing a retroviral vector which has been frozen and stored can be directly subjected to incubation at a temperature of less than 25° C. for 4 hours or more. That is, an additional step for thawing is not particularly required. In this case, it is desirable that the incubation in the step (a) be incubation with shaking. Examples of a general process for producing a retroviral vector include a process comprising introduction of a transfer vector carrying a foreign gene and a packaging signal into retrovirus packaging cells in which genes encoding retroviral structural proteins such as a gag-pol gene and an env gene are previously integrated into its chromosome, and a process comprising co-transfection of cells having no retroviral structural protein with the above-described transfer vector and a packaging plasmid having genes encoding retroviral structural proteins such as a gag-pol gene and an env gene.

The foreign gene to be transferred into the target cell can be used by being carried by a recombinant retroviral vector under the control of an appropriate promoter, for example, an LTR promoter present in the retroviral vector or a foreign promoter. In addition, another regulatory element (e.g., an enhancer sequence, a terminator sequence, or an intron sequence) which cooperates with a promoter and a transcription initiation site may be present in the vector in order to accomplish efficient transcription of the foreign gene. The foreign gene to be transferred into the target cell may be a naturally occurring gene or an artificially prepared gene. Alternatively, the foreign gene may be one in which DNA molecules of different origins are joined together by a known means such as ligation.

Any gene of which transfer into cells is desired can be selected as the foreign gene to be carried by a retroviral vector. For example, a gene encoding an enzyme or a protein associated with the disease to be treated, an intracellular antibody (see, for example, WO 94/02610), a T-cell receptor gene, a growth factor, an antisense RNA, an RNA causing RNA interference, a ribozyme, a false primer (see, for example, WO 90/13641) or the like can be used as the foreign gene. For example, a gene expressing MazF, which is a sequence specific ribonuclease, can be transferred into a CD4-positive T-cell as the foreign gene to obtain a CD4-positive T-cell showing anti-HIV activity (see, for example, WO 2007/020873 and WO 2008/133137). Furthermore, a gene conferring sensitivity to a specific drug, e.g., a thymidine kinase gene, can be transferred into a cell to obtain a cell having sensitivity to the drug.

The retroviral vector used in the present invention may contain a suitable marker gene that enables the selection of gene transferred cells. For example, a drug-resistance gene that confers resistance to antibiotics on cells, a reporter gene that makes it possible to distinguish the gene transferred cells by detecting enzymatic activity or fluorescence, a cell surface marker gene localized on the cell surface or the like can be utilized as the marker gene. When a neomycin phosphotransferase gene is used as the marker gene, gene transferred cells can be confirmed based on their resistance to G418 as a marker, isolated, and purified. When a gene encoding an extracellular domain of a low affinity nerve growth factor receptor (LNGFR) is used as the cell surface marker gene, gene transferred cells can be isolated and purified by utilizing an anti-LNGFR antibody.

Examples of the retroviral vector that can be used in the present invention include vectors such as MFG vector (ATCC No. 68754), α-SGC vector (ATCC No. 68755) and LXSN vector [BioTechniques, vol. 7, pp 980-990 (1989)], DON-5, DON-AI-2, and MEI-5 retroviral vectors and pLVSIN-CMV lentiviral vectors manufactured by TAKARA BIO INC., RETRO-X Q™ vector series and LENTI-X™ vector series manufactured by Clontech, and the like.

The vectors can be prepared by using known packaging cell lines such as PG13 (ATCC CRL-10686), PA317 (ATCC CRL-9078), GP+E-86 (ATCC CRL-9642), GP+envAm12 (ATCC CRL-9641), and ψCRIP [Proc. Natl. Acad. Sci. USA, vol. 85, pp 6460-6464 (1988)]. The vectors can be also prepared by transiently transfecting 293T-cells (ATCC CRL-11268), G3T-hi cells (manufactured by TAKARA BIO INC.), or the like with a packaging plasmid expressing structural proteins of a recombinant virus and a retroviral vector plasmid, and then collecting the culture supernatant.

Known media such as Dulbecco's Modified Eagle's Medium and Iscoves Modified Dulbecco's Medium can be used for culturing virus-producing cells which are produced by transferring a retroviral vector into packaging cells, or for culturing target cells. Such media are commercially available, for example, from Gibco. Various constituents can be added to these media depending on the type of the target cells for gene transfer or other purposes. For example, serum, various cytokines, or reducing agents can be added to the media in order to promote or suppress the growth or the differentiation of target cells. For example, calf serum (CS), fetal calf serum (FCS), human serum or the like can be used as the serum. In place of serum, serum replacement or purified serum albumin (e.g., human serum albumin) can be also used. The cytokines include interleukins (IL-2, IL-3, IL-4, IL-6, etc.), colony-stimulating factors (G-CSF, GM-CSF, etc.), stem cell factor (SCF), erythropoietin, and various cell growth factors, and many of these cytokines derived from humans are commercially available. For use of cytokines, cytokines having the suitable activity for the purposes are selected. Optionally, cytokines may be used in combination. When viruses are collected, a culture medium may be replaced with a medium suitable for culturing target cells. For example, when the target cell is a human lymphocyte, GT-T503™ medium, GT-T-RETROI™ medium, GT-T-RETROIII™ medium (all manufactured by TAKARA BIO INC.), X-VIVO15™ medium (manufactured by LONZA), or AIM-V® medium (manufactured by Invitrogen) which is suitable for culturing lymphocyte can be used.

It is known that addition of sodium butyrate during the cultivation of virus-producing cells increases the amount of virus particles produced in the supernatant [Human Gene Therapy, vol. 6, pp 1195-1202 (1995)]. The high-titer virus supernatant thus prepared can be used in the gene transfer method of the present invention, without problems.

Examples of the virus titer of the liquid containing a retroviral vector used in the step (a) include, but not limited to, $10^7$ copies/mL or more, preferably from $10^8$ to $10^{12}$ copies/mL, and more preferably from $10^9$ to $10^{12}$ copies/mL. The above-described virus titer is a calculation result based on the RNA copy number measured using Retrovirus Titer Set (for Real Time PCR) manufactured by TAKARA BIO Inc. In the case of describing the biological titer showing virus infectivity, the titer is from $1/10^2$ to $1/10^3$ of the above-described numerical value.

The retrovirus-binding substance used in the present invention is not particularly limited as long as the substance shows binding affinity to retroviruses, and examples thereof include at least one substance selected from fibronectin, fibroblast growth factor, collagen type V, polylysine and DEAE-dextran, as well as fragments thereof. These substances can be chemically modified to enhance the activity of binding to retroviruses (for example, Patent Literature 2).

The retrovirus-binding substance may also have a cell-binding activity, or the retrovirus-binding substance may be used in combination with a cell-binding substance. The cell-binding substance is not particularly limited as long as the substance shows binding affinity to cells, and for example, it is selected from cell-adhesive proteins, hormones, cytokines, antibodies, sugar chains, carbohydrates, metabolites, and the like. An antibody that specifically binds to a target cell is useful for specifically transferring a gene into a specific cell. The antibody that can be used in the present invention is not particularly limited. An antibody against an antigen expressed on a target cell into which a gene is to be transferred can be appropriately selected for use. A gene can be transferred into a target cell with high specificity by using an antibody that recognizes a CD antigen expressed on the target cell. For example, gene transfer can be directed to helper T-cells by using an anti-CD4 antibody, to killer T-cells by using an anti-CD8 antibody, or to hematopoietic stem cells by using an anti-CD34 antibody. The antibody can be produced according to known methods. Currently, many antibodies are commercially available, and they can also be used. The antibody may be a polyclonal antibody or a monoclonal antibody as long as it has desired properties such as cell specificity. Additionally, an antibody or a derivative of an antibody modified using known techniques such as a humanized antibody, a Fab fragment or a single-chain antibody may also be used.

Proteins having a cell adhesion activity (fibronectin, laminin, thrombospondin, vitronectin, etc.), fragments thereof containing a cell binding domain, and various glycoproteins, and sugar chains thereof (e.g., high mannose type N-linked sugar chain) can be also used as the cell-binding substance.

Furthermore, the cell-binding substance attached to the retrovirus-binding substance can be preferably used for gene transfer.

The above-described substances can be obtained from naturally occurring substances, prepared artificially (for example, by recombinant DNA techniques or chemical synthesis techniques), or prepared by combining a naturally occurring substance and an artificially prepared substance. For gene transfer using the above-described substances, a mixture of a substance that has a retrovirus-binding site and another substance that has a cell-binding site, or a substance that has a retrovirus-binding site and a cell-binding site can be also used, as described in WO 97/18318. As the above-described substances, substances substantially free of other proteins naturally associated therewith are used.

Fibronectin and fragments thereof are preferably used as the substance having both a retrovirus-binding activity and a cell-binding activity. The fibronectin and fragments thereof can be prepared in a substantially pure form from naturally occurring materials according to a method as described, for example, in J. Biol. Chem., vol. 256, p 7277 (1981), J. Cell. Biol., vol. 102, p 449 (1986), or J. Cell. Biol., vol. 105, p 489 (1987). The fibronectin and fragments thereof can be also prepared using recombinant DNA techniques as described in U.S. Pat. No. 5,198,423. Specifically, a fibronectin fragment containing heparin-II domain, which is a retrovirus-binding site, such as recombinant polypeptides including fibronectin fragments CH-296, H-271, H-296 and CH-271 as well as the method for obtaining them are described in detail in U.S. Pat. No. 5,198,423. Among the fibronectin fragments as described above, H-296 has a polypeptide of a region binding to VLA-4, CH-271 has a peptide of a region binding to VLA-5, and CH-296 has both of them [Nature Medicine, vol. 2, pp 876-882 (1996)]. CH-296 is commercially available under a registered trademark of RETRONECTIN® (recombinant human fibronectin fragment).

Examples of the culture vessel used in the present invention include, but not limited to, a bag for cell culture, a plate for cell culture, a petri dish for cell culture, a test tube for cell culture, and a flask for cell culture. The material of the culture vessel is not particularly limited, and for example, a plastic or glass culture vessel can be used in the present invention. When gene transfer into a large amount of cells is desired, a bag for cell culture, particularly a gas-permeable bag for cell culture is preferably used in the present invention. In the case of immobilizing a retrovirus-binding substance on the inner surface of a culture vessel, examples of the material of the culture vessel used include, but not limited to, polystyrene, polyethylene, cycloolefin resin, and fluorine resin.

A method of immobilizing a retrovirus-binding substance to a culture vessel can be appropriately selected depending on the type of the substance and the type of the culture vessel used. For example, when the substance having a retrovirus-binding activity is polypeptide, it can be immobilized to the surface of the culture vessel by physisorption. The substance having a retrovirus-binding activity may be also immobilized to the culture vessel through covalent bonds using a cross-linking agent or the like.

The temperature condition of incubation in the step (a) is not particularly limited as long as the temperature is less than 25° C., and examples thereof include a temperature of less than 20° C., preferably less than 18° C., more preferably from 1° C. to 18° C., and further more preferably from 1° C. to 10° C. The incubation time is not particularly limited as long as it is 4 hours or more, and examples thereof include more than 5 hours and not more than 72 hours, preferably more than 5 hours and not more than 48 hours, more preferably from 6 hours to 48 hours, further more preferably from 8 hours to 48 hours, and still further more preferably from 12 hours to 48 hours, from the viewpoint of gene transfer efficiency. The incubation time is, for example, 40 hours or less, 35 hours or less, 30 hours or less, 25 hours or less, 20 hours or less, or 18 hours or less. In addition, the incubation time is, for example, 4 hours or more, 6 hours or more, 8 hours or more, 12 hours or more, 16 hours or more, 18 hours or more, 20 hours or more, or 24 hours or more. The amount of a virus liquid to be incubated in the step (a) is, for example, from 0.5 mL to 1000 mL.

Although the incubation may be carried out in a state of standing still, the binding efficiency of a retroviral vector to a culture vessel can be increased by incubation with shaking. The shaking can be performed by, for example, horizontal reciprocating (to-and-fro) or orbital shaking of the culture vessel, seesaw-like shaking providing an inclination to the culture vessel, or a combination thereof. Various apparatuses for carrying out such shaking are commercially available. The shaking conditions are particularly limited as long as the liquid containing a retroviral vector can move in the culture vessel depending on the shape and size of the culture vessel used. For example, in the case of shaking by seesaw-like shaking with an inclination angle of 9°, the shaking rate is preferably from 20 rpm to 75 rpm, more preferably from 30 rpm to 70 rpm, and further more preferably from 30 rpm to 65 rpm. The inclination angle of the shaking may be appropriately adjusted in the range of 0° to 15°, which does not particularly limit the present invention. In the case of horizontal reciprocating shaking, the shaking rate is for example from 30 rpm to 300 rpm, preferably from 35 rpm to 280 rpm, and more preferably from 40 rpm to 260 rpm.

When in the step (a), a bag for cell culture is used as the culture vessel and incubation with shaking is carried out, the volume of a virus liquid to be injected into the bag can be appropriately determined considering mobility of the virus liquid in the bag on shaking and the like. The volume of a virus liquid injected into a bag for cell culture is, for example, from 5 mL to 1000 mL, preferably from 50 mL to 700 mL, and more preferably from 100 mL to 500 mL. For example, when a bag for cell culture permitting high mobility of a solution in the bag on shaking is used, sufficient mobility of the virus liquid in the bag on shaking can be secured by injecting into the bag an appropriate amount of a virus liquid depending on the volume of the bag. When a bag for cell culture permitting low mobility of a solution in the bag on shaking is used, mobility of a virus liquid in the bag on shaking is increased by injecting into the bag sterile air together with the virus liquid and thereby the preloading efficiency can be increased, as described in Example 6. The ratio of the injected virus liquid to the injected sterile air is, for example, from 3:1 to 2:1. The gene transfer method of the present invention is suitable for preparation of a large amount of gene transfered cells because highly efficient gene transfer can be realized in large scale gene transfer using a bag for cell culture, as shown in Example 9.

When in the step (a), a large scale bag with a culture area of about 200 cm$^2$ or more is used as the culture vessel and incubation with shaking is carried out as described in Example 9, it is preferred that the shaking rate be from 30 to 70 rpm for horizontal reciprocating shaking with an inclination angle of 0° or the shaking rate be from 25 to 45 rpm for seesaw-type shaking with an inclination angle of 3 to 5° (particularly)4°, and the incubation temperature be in the range of 1° C. to 10° C., which the present invention is not limited to. The incubation time is preferably from 8 hours to 20 hours.

When the present invention is carried out using a bag for cell culture, a retroviral vector is bound to the whole inner surface of the bag. It is preferable to avoid contact between the inner surfaces of the bag because it may detach the bound retroviral vector. For example, the detachment of a retroviral vector as described above can be avoided by holding the bag between hard plate-like products.

After the incubation, the liquid containing a retroviral vector may be replaced with a fresh liquid containing a retroviral vector and further incubation may be carried out, as described in Example 2 set forth below. Alternatively, after the incubation, to the liquid containing a retroviral vector, a fresh liquid containing a retroviral vector may be added, and further incubation may be carried out. After carrying out the step (a), the step (b1) of "washing the culture vessel obtained by the step (a)" set forth below is carried out, and then the step (a) may be repeated again. Thereby the gene transfer efficiency can be further improved.

As shown in Example 10 set forth below, when the liquid in the culture vessel is recovered after the incubation in the step (a), retroviral vectors maintaining infectability remain in the recovered liquid. The recovered liquid can be reused for the gene transfer method of the present invention. If the recovered liquid containing a retroviral vector is directly used or a mixture of the recovered liquid containing a retroviral vector and an unused liquid containing a retroviral vector is used for the gene transfer method of the present invention, the amount used of the virus can be reduced, and thus an economic advantage is provided.

The binding efficiency of a retroviral vector to a culture vessel can be confirmed, for example, by measuring the rate of gene-transferred cells in cells finally obtained by the method of the present invention (gene transfer efficiency) or the copy number of provirus in cells finally obtained by the method of the present invention. The gene transfer efficiency can be measured by a known method. For example, when a marker gene encoding a fluorescent protein such as ZsGreen as the foreign gene is transferred into cells, the gene transfer efficiency can be measured by counting the number of cells having the transgene with a flow cytometer. When a gene encoding a gene product expressed on the cell surface is used as the foreign gene, the gene transfer efficiency can be measured with a flow cytometer as the above by utilizing a labeled antibody specifically binding to the gene product.

By the step (b) of "adding a target cell into the culture vessel obtained by the step (a), followed by incubation", the target cell is infected with the retroviral vector, and thus cells into which the foreign gene is transferred can be efficiently obtained. The incubation can be performed by a conventional method for infection of a cell with a retroviral vector. For example, the incubation is performed in a medium suitable for the target cells under the conditions of 35° C. to 40° C. (e.g., 37° C.) and a carbon dioxide concentration of 2 to 10% (e.g., 5%). The incubation conditions and time can be appropriately varied depending on the type of target cells or the purpose. For example, the incubation time is from 4 hours to 96 hours. In the case of using a bag for cell culture as the culture vessel, a retroviral vector is bound to both sides of the inner surface of the bag by the step (a). Then, in the step (b), a target cell is added into the bag, followed by incubation for a certain period of time, and thereafter, the bag is turned upside down and further incubated for a certain period of time to promote infection of the target cells with the retroviral vectors on both inner surfaces of the bag, whereby the gene transfer efficiency can be further improved.

When an oncoretrovirus-based vector is used as the retroviral vector, it cannot transfer a foreign gene into the chromosomal DNA of cells in $G_0$ phase. In this case, it is preferable to lead the target cell into the cell cycle by pre-stimulation with a growth factor suitable for the target cell. For example, various cytokines such as interleukin-3, interleukin-6, and stem cell factors can be used to pre-stimulate bone marrow cells or hematopoietic stem cells for gene transfer. When a lentiviral vector is used, pre-stimulation is not necessarily required.

It is known that receptors on the surfaces of cells are important in infection of the cells with retroviruses. For example, a basic amino acid transporter and a phosphate transporter are known to function as receptors for ecotropic viruses and amphotropic viruses, respectively [Proc. Natl. Acad. Sci. USA, vol. 93, pp 11407-11413 (1996)]. It is possible to make target cells susceptible to viral infection by pre-treating the cells in a medium containing decreased amounts of basic amino acids, phosphates, or salts or precursors thereof to activate the expression or metabolic turnover of the transporters.

Examples of a cell that can be used as the target for gene transfer by the method of the present invention include, but not limited to, stem cells (hematopoietic stem cells, mesenchymal stem cells, embryonic stem cells, etc.), hematopoietic cells, mononuclear cells (peripheral blood mononuclear cells, umbilical cord blood mononuclear cells, etc.), embryonic cells, primordial germ cells, oocytes, oogonia, ova, spermatocytes, sperms, erythroid precursor cells, lymphoid mother cells, mature blood cells, lymphocytes, B cells, T cells, NK cells, fibroblasts, neuroblasts, neurocytes, endothelial cells, vascular endothelial cells, hepatocytes, myoblasts, skeletal muscle cells, smooth muscle cells, cancer cells, myeloma cells, and leukemia cells. The method of the present invention is preferably utilized for hematopoietic cells derived from blood and bone marrow because these cells are relatively easy to obtain and because techniques for culturing and maintaining them are established. Particularly, when a long-term expression of the transferred gene in vivo is desired, pluripotent stem cells (hematopoietic stem cells, mesenchymal stem cells, etc.) and various precursor cells are suitable as the target cells. When a gene therapy is applied to AIDS, immune cells such as CD4-positive T-cells and precursor cells thereof are suitable as the target cells.

For example, a gene therapy using a CD4-positive T-cell as the target cell can be carried out by the following procedures. First, a material containing a CD4-positive T-cell, such as bone marrow tissue, peripheral blood or umbilical cord blood is collected from a donor. Such a material can be directly used in a gene transfer procedure. However, usually, the material is subjected to density-gradient centrifugation or the like to prepare a mononuclear cell fraction. Furthermore, purification of the cells using CD4 moleculesas a marker, removal of CD8-positive T-cells and/or monocytes, and a culture procedure for expanding the number of the CD4-positive T-cells may be carried out. The cell population thus obtained is infected with a recombinant retroviral vector carrying a gene of interest by the method of the present invention, after appropriate pre-stimulation (for example, stimulation with a CD3 ligand, a CD28 ligand, or IL-2) as necessary. The gene transferred cells thus obtained can be transplanted into a recipient, for example, by intravenous administration. Although the recipient is preferably the donor itself, allogenic transplantation can be also carried out.

Some of gene therapies using hematopoietic stem cells as the target cells are for complementing a deficient or abnormal gene in a patient, e.g., the gene therapy for ADA deficiency or Gaucher's disease. In addition, for example, a drug resistance gene may be transferred into hematopoietic stem cells in order to alleviate the damages of the hematopoietic cells due to chemotherapeutic agents used for the treatment of cancer or leukemia.

In addition, a method of giving lymphocytes cytotoxic activity specific to cancer cells expressing a tumor antigen by transferring a gene encoding a T-cell receptor recognizing the antigen is investigated as a gene therapy for cancer [Gene Therapy, vol. 15, p 695-699 (2008)]. Furthermore, attempts are made to treat AIDS using a gene therapy. In this case, it is considered that a gene encoding a nucleic acid molecule (e.g., single-strand specific endoribonuclease, an antisense nucleic acid, or a ribozyme) which interferes with the replication or gene expression of HIV, the causal agent of AIDS is transferred into T cells such as CD4-positive T-cells infected with HIV [e.g., WO 2007/020873, Human Gene Therapy, vol. 22, pp 35-43 (2011)].

Before adding a target cell in the step (b), if the liquid containing a retroviral vector contains undesired substances for gene transfer and cell culture, a step of "washing the culture vessel to which a retroviral vector is bound" may be performed to remove the undesired substances for gene transfer and cell culture. More specifically, a gene transfer method comprising the step (a) of "placing a liquid containing a retroviral vector carrying a foreign gene in a culture vessel on which a retrovirus-binding substance is immobilized, followed by incubation at a temperature of less than 25° C. for 4 hours or more to obtain the culture vessel to which the retroviral vector is bound", the step (b1) of "washing the culture vessel obtained by the step (a)", and the step (b2) of "adding a target cell into the culture vessel washed in the step (b1), followed by incubation" is also an aspect of the present invention.

In the step (b1) of "washing the culture vessel to which a retroviral vector is bound", for example, phosphate buffered saline, Hanks' saline, a liquid medium used for culturing a target cell and the like can be used. Furthermore, human serum albumin and the like can be appropriately added to the above-described saline or medium. By this step, undesired substances for gene transfer can be removed. Examples of the substances removed by the said step include retroviral infection-inhibitory substances derived from packaging cells contained in virus supernatants [Human Gene Therapy, vol. 8, pp 1459-1467 (1997), J. Viral., vol. 70, pp 6468-6473 (1996)], substances added during culturing retrovirus-producing cells in order to enhance retrovirus production, such as phorbol 12-myristate 13-acetate (TPA) and dexamethasone [Gene Therapy, vol. 2, pp 547-551 (1995)], as well as waste of cells, and sodium butyrate as described above.

EXAMPLES

Hereinafter, the present invention is further specifically described by way of examples. However, the present invention is not limited only to the following examples.

Example 1

Gene Transfer into SupT1 Cells by Various Virus Preloading Methods (1) Preparation of DON-ZsGreen Retroviral Vector pZsGreen Vector (manufactured by Clontech) was digested with restriction enzymes BamHI and EcoRI (manufactured by TAKARA BIO INC.), and subjected to agarose gel electrophoresis to recover an about 0.7 kbp fragment containing a sequence encoding green fluorescent protein ZsGreen. The recovered fragment was blunted using DNA Blunting Kit (manufactured by TAKARA BIO INC.), and then inserted into pDON-AI DNA (manufactured by TAKARA BIO INC.) to obtain a recombinant retroviral vector plasmid pDON-ZsGreen. Next, an ecotropic DON-ZsGreen virus was prepared using the recombinant retroviral vector plasmid pDON-ZsGreen and Retrovirus Packaging Kit Eco (manufactured by TAKARA BIO INC.). Thereafter, GaLV retrovirus packaging cell PG13 was infected with the ecotropic DON-ZsGreen virus. A virus-producing cell with high titer was cloned from the infected cell to establish a retroviral vector-producing cell line PG13/DON-ZsGreen. Furthermore, a GaLV/DON-ZsGreen virus solution (hereinbelow, referred to as DON-ZsGreen retroviral vector) was obtained by a conventional method using the producing cells in a medium containing 5 mM sodium butyrate. The resulting virus solution had an RNA titer of $1.88 \times 10^{10}$ copies/mL.

(2) Transfer of ZsGreen Gene into SupT1 Cells

To each well of a nontreated 24-well plate (manufactured by Becton Dickinson) was added 500 μL of 20 μg/mL CH-296 (product name: RETRONECTIN® (recombinant human fibronectin fragment); manufactured by TAKARA BIO INC.), which was a fibronectin fragment. The plate was incubated at 4° C. overnight and then washed twice with 500 μL of PBS. The plate thus prepared is referred to as a CH-296-coated plate in the Examples of the present specification. The plate was prepared as necessary.

The DON-ZsGreen retroviral vector prepared in Example 1-(1) was diluted 60-fold with an RPMI medium, and 1 mL of the diluted retroviral vector was added to each well of the CH-296-coated plate. The shaking conditions of the plate during preloading (binding of a retroviral vector to a culture vessel by RBV method) were studied for three types: no shaking (standing still) of the plate during preloading, shaking of the plate at 35 rpm and an inclination angle of 9° with a seesaw-type shaker [Mild Mixer, SI-36 (manufactured by TAITEC Co., Ltd.)], and shaking of the plate at 100 rpm, an inclination angle of 0° and a shaking width of 3 cm with a horizontal reciprocating shaker (Personal 10 INCUBATOR PERSONAL, manufactured by TAITEC Co., Ltd.). Preloading was carried out at an incubation temperature of 4° C. to 37° C. and an incubation time of 2 hours to 24 hours under each shaking condition. After the incubation, the virus solution was removed, and each well was washed with 1 mL of PBS containing 1.5% HSA per well. Subsequently, SupT1 cells (ATC CCRL-1942) were suspended at $5 \times 10^5$ cells/mL in a medium containing 10% FBS and 1% penicillin-streptomycin, added at 1 mL/well to the above-described virus-preloaded well, and then cultured in an incubator at 37° C. with 5% $CO_2$ to perform retrovirus infection (gene transfer by retroviral vector). On Day 1 after the start of the culture (Day 1 of the culture), the cell suspension was transferred to a fresh nontreated 24-well plate. Then, 4 mL/well of a medium containing 10% FBS and 1% penicillin-streptomycin was added to the plate to dilute the cell suspension 5-fold. The cell suspension was continuously cultured until Day 3 of the culture.

(3) Analysis of Gene Transfer Efficiency

Gene transfer efficiency was calculated as a rate of ZsGreen positive cells in the cells on Day 3 of the culture obtained in Example 1-(2) with a flow cytometer FACS CANTOII™ (manufactured by Becton Dickinson). Results are shown in Table 1.

TABLE 1

| Shaking Condition | Incubation Time (hr) | ZsGreen Positive Rate (%) | | |
|---|---|---|---|---|
| | | Temperature = 4° C. | Temperature = 16° C. | Temperature = 37° C. |
| Standing Still | 4 | 5.1 | 5.8 | 2.7 |
| | 8 | 6.9 | 8.1 | 2.4 |
| | 24 | 8.0 | 8.4 | 0.4 |
| 35 rpm | 2 | 5.8 | 4.9 | 3.3 |
| | 4 | 8.2 | 8.2 | 2.6 |
| | 6 | 11.5 | 12.2 | 1.1 |
| | 8 | 12.9 | 12.8 | 0.7 |
| | 24 | 14.8 | 12.4 | 0.3 |
| 100 rpm | 4 | 12.7 | ND | ND |
| | 8 | 17.7 | ND | ND |
| | 24 | 16.8 | ND | ND |

ND shows that no test was conducted.

As shown in Table 1, preloading at 4° C. or 16° C. for 4 hours or more resulted in high gene transfer efficiencies. Particularly, preloading at 4° C. or 16° C. for 6 hours or more by shaking resulted in high gene transfer efficiencies. By contrast, in the case of using a temperature of 37° C., preloading for 4 hours resulted in the highest gene transfer efficiency, and after that, the transfer efficiency was markedly lowered as the preloading time became longer. Further, regarding the shaking rate, horizontal reciprocating shaking at 100 rpm resulted in high transfer efficiencies.

Example 2

Gene Transfer into SupT1 Cells by Repeat of Shaking Preloading Method at 4° C.

(1) The DON-ZsGreen retroviral vector prepared in Example 1-(1) was diluted 30-fold with an RPMI medium, and 1 mL of the diluted retroviral vector was added to each well of a CH-296-coated plate. During preloading, the plate was subjected to horizontal reciprocating shaking at 100 rpm and an inclination angle of 0°. Two types of incubation times were used to experiment with two test conditions: incubation for 24 hours (24 hours test condition), and incubation for 16 hours, replacement of the incubated virus solution with 1 mL of a fresh virus solution and then incubation for further 8 hours (16+8 hours test condition) in order to investigate the effect of repeat of preloading. Both tests were conducted at an incubation temperature of 4° C. After the incubation, the virus solution was removed, and each well of the plate was washed using 1 mL/well of PBS containing 1.5% HSA. Subsequently, SupT1 cells were suspended at $5 \times 10^5$ cells/mL in a medium containing 10% FBS and 1% penicillin-streptomycin, added at 1 mL/well to the above-described virus-preloaded well, and then cultured in an incubator at 37° C. with 5% $CO_2$ to perform retrovirus infection. On Day 1 after the start of the culture (Day 1 of the culture), 0.4 mL of the cell suspension was transferred to a fresh nontreated 24-well plate. Then, 1.6 mL/well of a medium containing 10% FBS and 1% penicillin-streptomycin was added to the plate to dilute the cell suspension 5-fold. The cell suspension was continuously cultured until Day 3 of the culture.

(2) Analysis of Gene Transfer Efficiency

Gene transfer efficiency was calculated as a rate of ZsGreen positive cells in the cells on Day 3 of the culture obtained in Example 2-(1) with a flow cytometer FACS Cantoll (manufactured by Becton Dickinson). Results are shown in Table 2.

TABLE 2

| Shaking Condition | Incubation Time (hr) | Incubation Temperature (° C.) | ZsGreen Positive Rate (%) |
|---|---|---|---|
| 100 rpm | 24 | 4 | 21.7 |
|  | 16 + 8 | 4 | 42.3 |

As shown in Table 2, repeating the procedure of preloading under the shaking condition at 4° C. resulted in a gene transfer efficiency higher than that obtained by single preloading. In conclusion, an enrichment effect of the retroviral vector on the CH-296-coated vessel was brought about by repeating the procedure of preloading.

Example 3

Gene Transfer into SupT1 Cells by Various Closed Preloading Methods using Bag for Cell Culture (1) Into a culture bag with a culture area of 60 cm$^2$, CULTILIFE® (registered trademark) Spin (manufactured by Takara BIO Inc.), was injected 10 mL of 20 µg/mL CH-296. The culture bag was incubated at 4° C. overnight or longer, and then washed twice with 15 mL of PBS. The bag thus prepared (referred to as a CH-296-coated bag) was used in the following experiments.

The DON-ZsGreen retroviral vector prepared in Example 1-(1) was diluted 30-fold and 60-fold with an RPMI medium, and 30 mL of each diluted retroviral vector was injected into the CH-296-coated bag. The shaking conditions of the CH-296-coated bag during preloading were as follows: no shaking (standing still) of the bag during preloading, and horizontal reciprocating shaking of the bag at 100 rpm and an inclination angle of 0°. Preloading was carried out at an incubation temperature of 4° C. and an incubation time of 20 hours under each shaking condition. After the incubation, the virus solution was removed, and each bag was washed with 15 mL of PBS containing 1.5% HSA per bag. Subsequently, SupT1 cells were suspended at 5×10$^5$ cells/mL in a medium containing 10% FBS and 1% penicillin-streptomycin, added at 30 mL/bag to the above-described virus-preloaded bag, and then cultured for 3 days in an incubator at 37° C. with 5% CO$_2$ to perform retrovirus infection.

(2) Analysis of Gene Transfer Efficiency

Gene transfer efficiency was calculated as a rate of ZsGreen positive cells in the cells on Day 3 of the culture obtained in Example 3-(1) with a flow cytometer FACS CAN-TOII™ (manufactured by Becton Dickinson). Results are shown in Table 3.

TABLE 3

| Shaking Condition | Incubation Time (hr) | Incubation Temperature (° C.) | Dilution Rate of Vector (fold) | ZsGreen Positive Rate (%) |
|---|---|---|---|---|
| Standing Still | 4 | 37 | 60 | 2.1 |
|  | 4 | 37 | 30 | 3.5 |
| 100 rpm | 20 | 4 | 60 | 13.9 |
|  | 20 | 4 | 30 | 23.7 |

As shown in Table 3, preloading under the shaking condition at 4° C. resulted in high gene transfer efficiencies as compared with preloading at 37° C. for 4 hours. The results were equivalent to those shown in Table 1 of Example 1 wherein a 24-well plate was used as the culture vessel. Therefore, it was found that the capacity of the gene transfer method of the present invention could be easily scaled up 30 times.

Example 4

Gene Transfer into CD4-Positive T-Cell Population by Various Virus Preloading Methods (1) Preparation of Retroviral Vector carrying LNGFR and MazF Genes A retroviral vector carrying LNGFR and MazF genes was prepared as described in Examples 1 and 2 of WO 2008/133137. More specifically, a recombinant retroviral vector plasmid pMT-MFR-PL2 into which an HIV LTR-MazF cassette was inserted in the reverse direction to transcription of the retroviral vector genome and a gene encoding an extracellular domain of human low affinity nerve growth factor receptor was inserted downstream of a human PGK promoter in the forward direction was prepared and used to prepare an ecotropic MT-MFR-PL2 virus. Then, a GaLV retrovirus packaging cell PG13 was infected with the ecotropic MT-MFR-PL2 virus, and a virus-producing cell with high titer was cloned to establish a retroviral vector-producing cell line PG13/MT-MFR-PL2. Furthermore, a GaLV/MT-MFR-PL2 virus solution was obtained by a conventional method using the producing cells in a medium containing 5 mM sodium butyrate. The resulting virus solution had an RNA titer of 6.6×10$^9$ copies/mL.

(2) Preparation of CD4-Positive T-Cell Population

Human peripheral blood mononuclear cells (PBMCs) were prepared according to a conventional method from healthy human donors TK19 and TK29 after obtaining informed consent. PBMCs were suspended at 1×10$^7$ cells/mL in PBS containing 2 mM EDTA and 0.1% BSA (hereinafter, referred to as Buffer 1). Thereafter, CD8-positive selection beads (DYNABEADS® M-450 CD8: manufactured by Invitrogen) washed with Buffer 1 were added at 2×10$^7$ beads per 1×10$^7$ cells of PBMCs. After gently stirring at 4° C. for 30 minutes with a rotator, the cell suspension containing the beads was allowed to stand still on a magnetic separator MPC-15 (manufactured by Dynal) for 2 to 3 minutes, and then, beads-unbound cells were collected (hereinafter, referred to as a CD8-depleted cell population). The collected CD8-depleted cell population was centrifuged at 500×g for 5 minutes, and then suspended at 5×10$^5$ cells/mL in a medium for culturing lymphocyte based on X-VIVO15™ (manufactured by LONZA) (hereinafter, referred to as X-VIVO15CM).

(3) Gene Transfer into the Cell Population Prepared in Example 4-(2) and Expansion Culture (3)-1 Preloading of Retroviral Vector Preloading of a viral vector was carried out by three methods of: a shaking condition at 4° C. for 19 hours, a shaking condition at 37° C. for 4 hours, and a centrifugation condition at 32° C. for 3 hours. More specifically, 1 mL of the GaLV/MT-MFR-PL2 virus solution prepared in Example 2-(1) was added to each well of a CH-296-coated plate, and preloading of the retroviral vector was carried out by shaking at 4° C. for 19 hours, shaking at 37° C. for 4 hours, or centrifugation at 32° C., 2000×g for 3 hours. The shaking was performed at an inclination angle of 9° and a shaking rate of 35 rpm with a seesaw-type shaker, Mild Mixer, SI-36. Thereafter, the supernatant was removed, and each well was washed using 1 mL of PBS containing 1.5% HSA per well. The preloaded plate thus prepared was maintained at 4° C. until use.

(3)-2 Start of Culture

To a flask for cell culture with a base area of 25 cm² (manufactured by Corning Incorporated) was added 10 mL of the CD8-depleted cell population prepared in Example 4-(2). The amount of DYNABEADS® Human T-Activator CD3/CD28 (selection beads, manufactured by Invitrogen) that was 3 times the cell number was dispensed into a centrifuge tube, washed with X-VIVO15™, and then added to the flask containing the cells. The flask was placed upright in an incubator at 37° C. and 5% $CO_2$ and culture was started (Day 0 of the culture).

(3)-3 Gene Transfer

On Day 3 of the culture, the cells were collected into a centrifuge tube and centrifuged at 500×g for 5 minutes. After the supernatant was removed, X-VIVO15CM was added to the tube at 5×10⁵ cells/mL and suspended. After the supernatant in the preloaded plate prepared in Example 3-(3)-1 was removed, 1 mL of the cell suspension was added to each well of the plate, and then incubated in an incubator at 37° C. and 5% $CO_2$ to perform retrovirus infection of the cells. For an uninfected condition, the same procedures as described above were carried out except that a CH-296-coated plate was used in place of the preloaded plate.

(3)-4 Expansion Culture

On Day 4 of the culture, the cells infected with the retrovirus in Example 4-(3)-3 were collected into a centrifuge tube and centrifuged at 500×g for 5 hours. After the supernatant was removed, the cells were suspended in 2 mL of X-VIVO15CM and cultured at 2-fold dilution. Furthermore, on Day 5 of the culture, X-VIVO15CM containing Human AB Serum (manufactured by LONZA) at a final concentration of 5% was added to the cells, and 5-fold dilution culture was performed until Day 7 of the culture.

(4) Analysis of Gene Transfer Efficiency

The cells on Day 7 of the culture obtained in Example 4-(3) were washed with 0.1% BSA/PBS. Subsequently, the cells were suspended in 0.1% BSA/PBS. To the cell suspension was added an antibody solution containing an FITC-labeled mouse anti-human CD8 antibody (manufactured by Becton Dickinson), a PerCP-labeled mouse anti-human CD3 antibody (manufactured by Becton Dickinson), an APC-labeled mouse anti-human LNGFR antibody (manufactured by Miltenyi Biotec), and an APC-Cy7-labeled mouse anti-human CD4 antibody (manufactured by Becton Dickinson) as an antibody reaction solution, to perform an antibody reaction. Thereafter, the cells were washed twice with 0.1% BSA/PBS, and again suspended in 0.1% BSA/PBS. The cells were subjected to flow cytometry, and gene transfer efficiency was calculated as a rate of LNGFR positive cells in CD3-positive CD4-positive cells of each cell population. Results are shown in Table 4.

TABLE 4

| | LNGFR Positive Rate (%) | |
|---|---|---|
| Test Condition | TK19 | TK29 |
| Uninfected Condition | 0 | 0.1 |
| Shaking Condition at 4° C. for 19 hours | 59.5 | 67.5 |
| Shaking Condition at 37° C. for 4 hours | 24.0 | 34.3 |
| Centrifugation Condition at 32° C. for 3 hours | 29.6 | 37.9 |

As a result, it was demonstrated that the shaking condition at 4° C. for 19 hours resulted in the highest gene transfer efficiency, which was much higher than that in the centrifugation condition at 32° C. for 3 hours, in the case of each donor.

Example 5

Gene Transfer into CD4-Positive T-Cells Population by Shaking Virus Preloading Method (1) Preparation of Retroviral Vector A GaLV/MT-MFR-PL2 virus solution was obtained by a conventional method using the retroviral vector producing cell line PG13/MT-MFR-PL2 described in Example 4-(1) in a culture medium containing or not containing 5 mM sodium butyrate. Herein, the RNA titers of the resulting virus solutions are shown in Table 5 below.

TABLE 5

| | RNA Titer (copy/mL) |
|---|---|
| Sodium Butyrate-added Virus Solution | $4.69 \times 10^9$ |
| Sodium Butyrate-non-added Virus Solution | $1.33 \times 10^9$ |

(2) Preparation of CD8-Depleted Cell Population

A CD8-depleted cell population was prepared from a healthy human donor TK19 after obtaining informed consent in the same manner as in Example 4-(2). The cell population was suspended at 5×10⁵ cells/mL in X-VIVO15CM.

(3) Gene Transfer into Cell Population Prepared in Example 5-(2) and Expansion Culture (3)-1 Preloading of Retroviral Vector Preloading of a viral vector was carried out by shaking at 4° C. for 30 hours. More specifically, 0.7 mL of the GaLV/MT-MFR-PL2 virus solution containing or not containing sodium butyrate prepared in Example 5-(1) was added to each well of a CH-296-coated plate which was obtained by the same manner as in Example 1-(2). Preloading of the retroviral vector was carried out by shaking at 4° C. for 30 hours. The shaking was performed at an inclination angle of 9° and a shaking rate of 35 rpm using a seesaw-type shaker Mild Mixer, SI-36. After the preloading, the virus solution was removed and each well of the plate was washed using 1 mL of PBS containing 1.5% HSA per well (virus-washed condition) or the virus solution was not removed (virus-unwashed condition). The preloaded plate thus prepared was maintained at 4° C. until use.

(3)-2 Start of Culture

To a flask for cell culture with a base area of 25 cm² (manufactured by Corning Incorporated) was added 12 mL of the CD8-depleted cell population prepared in Example 5-(2). The amount of DYNABEADS® Human T-Activator CD3/CD28 (selection beads, manufactured by Invitrogen) that was 3 times the cell number was washed with X-VIVO15™, and then added to the flask containing the cells. The flask was placed upright in an incubator at 37° C. and 5% $CO_2$ and culture was started (Day 0 of the culture).

(3)-3 Gene Transfer

On Day 3 of the culture, the cells were collected into a centrifuge tube and centrifuged at 500×g for 5 minutes. After the supernatant was removed, X-VIVO15CM was added to the tube at 7.14×10⁵ cells/mL and suspended. For the virus-washed condition, the supernatant in the preloaded plate prepared in Example 5-(3)-1 was removed, 0.7 mL of the cell suspension was added to each well of the plate, and then 0.3 mL of X-VIVO15CM was added per well (a final density of 5×10⁵/well). For the virus-unwashed condition, 0.7 mL of the cell suspension was added to each well of the plate containing the virus solution (a final density of $5\times10^5$/well). The plates were incubated in an incubator at 37° C. and 5% $CO_2$ to perform retrovirus infection of the cells (first time infection).

Furthermore, on Day 4 of the culture, the cells were collected into a centrifuge tube and centrifuged at 500×g for 5 minutes. After the supernatant was removed, each cells were suspended in 0.7 mL of X-VIVO15CM to perform retrovirus infection in the same manner as in Day 3 of the culture (second time infection).

(3)-4 Expansion Culture

On Day 5 of the culture, X-VIVO15CM containing Human AB Serum (manufactured by LONZA) at a final concentration of 5% was added to the cells and 5-fold dilution culture was performed until Day 7 of the culture. Furthermore, on Day 7 of the culture, X-VIVO15CM containing Human AB Serum (manufactured by LONZA) at a final concentration of 5% was added to the cells and 4-fold dilution culture was performed until Day 10 of the culture. For the uninfected condition, the same procedures as in Example 5-(3)-2 to Example 5-(3)-4 were carried out except that a CH-296-coated plate was used in place of the preloaded plate. The fold expansion of each test condition is shown in Table 6.

TABLE 6

| Test Condition | Expansion Fold |
| --- | --- |
| Uninfected Condition | 95.3 |
| Sodium Butyrate-added Virus Solution: Virus-Washed Condition | 92.0 |
| Sodium Butyrate-added Virus Solution: Virus-Unwashed Condition | 18.2 |
| Sodium Butyrate-non-added Virus Solution: Virus-Washed Condition | 85.3 |
| Sodium Butyrate-non-added Virus Solution: Virus-Unwashed Condition | 90.3 |

As a result, when a sodium butyrate-added virus solution was used, cell proliferation was inhibited unless the virus solution was washed. By contrast, when a sodium butyrate-non-added virus solution was used, an expansion culture rate equivalent to that in the uninfected condition was shown even without washing of the virus solution.

(4) Analysis of Gene Transfer Efficiency

The cells on Day 10 of the culture obtained in Example 5-(3) were washed with 0.1% BSA/PBS. Subsequently, the cells were suspended in 0.1% BSA/PBS. To the cell suspension was added an antibody solution containing an FITC-labeled mouse anti-human CD8 antibody (manufactured by Becton Dickinson), a PerCP-labeled mouse anti-human CD3 antibody (manufactured by Becton Dickinson), an APC-labeled mouse anti-human LNGFR antibody (manufactured by Miltenyi Biotec), and an APC-Cy7-labeled mouse anti-human CD4 antibody (manufactured by Becton Dickinson) as an antibody reaction solution, to perform an antibody reaction. Thereafter, the cells were washed twice with 0.1% BSA/PBS, and again suspended in 0.1% BSA/PBS. The cells were subjected to flow cytometry, and gene transfer efficiency was calculated as a rate of LNGFR positive cells in CD3-positive CD4-positive cells of each cell population. Results are shown in Table 7.

TABLE 7

| Test Condition | LNGFR Positive Rate (%) |
| --- | --- |
| Uninfected Condition | 0.3 |
| Sodium Butyrate-added Virus Solution: Virus-Washed Condition | 60.7 |
| Sodium Butyrate-added Virus Solution: Virus-Unwashed Condition | 52.5 |
| Sodium Butyrate-non-added Virus Solution: Virus-Washed Condition | 46.7 |
| Sodium Butyrate-non-added Virus Solution: Virus-Unwashed Condition | 52.8 |

As a result, the condition where virus preloading was performed using a sodium butyrate-added virus solution and the virus solution was washed had the highest gene transfer efficiency. In the case where a sodium butyrate-non-added virus was used, the equivalent level of gene transfer could be attained though it was inferior to the case where a sodium butyrate-added virus was used.

Example 6

Gene Transfer into SupT1 Cells by Preloading Method in Closed System Using Bag for Cell Culture (1) Preparation of Retroviral Vector Carrying MazF Gene A retroviral vector carrying MazF gene was prepared as described in Examples 1 and 2 of WO 2008/133137. More specifically, a recombinant retroviral vector plasmid pMT-MFR3 into which an HIV LTR-MazF cassette was inserted in the reverse direction to transcription of the retroviral vector genome was prepared and used to prepare an ecotropic MT-MFR3 virus. Then, a GaLV retrovirus packaging cell PG13 was infected with the ecotropic MT-MFR3 virus, and a virus-producing cell with high titer was cloned to establish a retroviral vector-producing cell line PG13/MT-MFR3. Furthermore, the retroviral producing cells were cultured at 32° C. for 24 hours in a GT-T-Retrol medium (manufacture By TAKARA BIO INC.) containing 5 mM sodium butyrate. The resulting culture supernatant was collected to obtain a GaLV/MT-MFR3 virus solution. The resulting virus solution had an RNA titer of $1.4\times10^{10}$ copies/mL.

(2) Transfer of MazF Gene into SupT1 Cells

To a gas permeable culture bag PERIVIALIFE™ PL30 (manufactured by OriGen Biomedical) was added 9 mL/bag of 20 μg/mL CH-296. The bag was incubate overnight at 4° C., and then washed twice with 15 mL of PBS. The bag thus prepared (referred to as a CH-296-coated bag) was used in the following experiments.

The MT-MFR3 retrovirus solution prepared in Example 6-(1) was diluted 2-fold with a GT-T-Retrol medium. The preloading conditions were studied for three types: injection of the diluted virus solution into a CH-296-coated bag followed by shaking for 16 hours or 24 hours, and injection of 25 mL of the viral vector and 10 mL of sterile air into a CH-296-coated bag followed by shaking for 16 hours. The shaking was performed at a shaking rate of 100 rpm, an inclination angle of 0° and a shaking width of 2.5 cm using a horizontal reciprocating shaker (MMS-3010: manufactured by TOKYO RIKAKIKAI CO, LTD.). After the incubation, the virus solution was removed, the bag was washed with 15 mL/bag of PBS containing 1.5% HSA. Subsequently, 25 mL of SupT1 cell suspension prepared so as to be $5\times10^5$ cells/mL using an RPMI1640 medium containing 10% FBS and 1% penicillin-streptomycin was injected into the above-described virus-preloaded bag, and then cultured for 24 hours in an incubator at 37° C. and 5% $CO_2$. Next, the cells under each test condition were suspended, diluted 5-fold using an RPMI1640 medium containing 10% FBS and 1% penicillin-streptomycin, and then cultured for further 2 days.

(3) Analysis of Gene Transfer Efficiency

Genomic DNA was extracted from the cells obtained in Example 6-(2) that were equivalent to $1×10^6$ cells using FASTPURE® (registered trademark) DNA purification Kit (manufactured by TAKARA BIO INC.). The number of transferred vector copies was measured using Provirus Copy Number Detection Primer Set, Human (for Real Time PCR) (manufactured by TAKARA BIO INC.). Results are shown in Table 8 below.

TABLE 8

| Incubation Time (hr) | Injection Amount of Virus Solution (mL) | Injection Amount of Air (mL) | Number of Transferred Vector Copies/Cell |
|---|---|---|---|
| 16 | 25 | 0 | 1.26 |
| 24 | 25 | 0 | 1.24 |
| 16 | 25 | 10 | 2.18 |

The material of PERMALIFE™ PL30% culture bag) is hard as compared to those of other bags. When only the virus solution was injected into the PERMALIFE™ PL30 bag (culture bag) and the bag was closed, movement of the solution contained in the bag on shaking was small. However, when the virus solution and air were injected into the bag, movement of the solution contained in the bag became larger. In addition, as shown in Table 8, when into the closed bag for cell culture were injected the virus solution and air, the efficiency of preloading was improved.

Example 7

Study of Incubation Time (Plate Infection)

(1) Transfer of MazF Gene into SupT1 Cells

An MT-MFR3 retrovirus solution prepared in the same manner as in Example 6-(1) was diluted 2-fold with a GT-T-RetroI medium, and 1 mL of the diluted solution was added to each well of a CH-296-coated plate. The preloading conditions were shaking for 12, 16, 24, 48 and 72 hours after injection of 1 mL of the diluted virus solution into the CH-296-coated plate. The shaking was performed at a shaking rate of 100 rpm, using a horizontal reciprocating shaker (MMS-3010: manufactured by TOKYO RIKAKIKAI CO, LTD.) at an inclination angle of 0° and a shaking width of 2.5 cm. After the incubation, the virus solution was removed, and the plate was washed with 0.5 mL/well of PBS containing 1.5% HSA. Subsequently, 1 mL of SupT1 cell suspension prepared so as to be $5×10^5$ cells/mL using an RPMI1640 medium containing 10% FBS and 1% penicillin-streptomycin was injected into the above-described virus-preloaded plate, and then cultured for 24 hours in an incubator at 37° C. and 5% $CO_2$. Next, the cells under each test condition were suspended and diluted 5-fold using an RPMI1640 medium containing 10% FBS and 1% penicillin-streptomycin, and then cultured for further 2 days.

(2) Analysis of Gene Transfer Efficiency

Using the cells obtained in Example 7-(1) that were equivalent to $1×10^6$ cells, the number of transferred vector copies was measured in the same manner as in Example 6-(3). Results are shown in Table 9 below.

TABLE 9

| Incubation Time (hr) | Number of Transferred Vector Copies/Cell |
|---|---|
| 12 | 1.19 |
| 16 | 1.63 |
| 24 | 1.43 |
| 48 | 1.21 |
| 72 | 0.84 |

As a result, the gene transfer efficiency by the MT-MFR3 retroviral vector was the highest at an incubation time of 16 hours, and a transfer efficiency of 1 copy/cell or more could be realized at an incubation time from 12 to 48 hours.

Example 8

Study of Incubation Time (Small Scale Bag Infection)

(1) Transfer of MazF Gene into SupT1 Cells

An MT-MFR3 retrovirus solution prepared in the same manner as in Example 6-(1) was diluted 4-fold with a GT-T-RetroI medium, and 25 mL of the diluted solution was injected into a CH-296-coated bag which was prepared in the same manner as in Example 6-(2) using a gas permeable culture bag PERIVIALIFE™ PL30 (manufactured by Ori-Gen Biomedical). Furthermore, 10 mL of sterile air was injected into the bag, followed by incubation. For a control, 1 mL of the 4-fold diluted retrovirus solution was added to each well of a CH-296-coated plate, followed by incubation. The preloading conditions were shaking for 12, 16, and 24 hours for the PL30 bag, and shaking for 16 hours for the plate. The shaking was performed at a shaking rate of 100 rpm, using a horizontal reciprocating shaker at an inclination angle of 0° and a shaking width of 2.5 cm. After the incubation, the virus solution was removed, and the bags and plate were washed with 15 mL/bag and 0.5 mL/well of the plate of PBS containing 1.5% HSA. Subsequently, SupT1 cell suspension prepared so as to be $4×10^5$ cells/mL using an RPMI1640 medium containing 10% FBS and 1% penicillin-streptomycin was injected in amounts of 25 mL/bag and 1 mL/well into the above-described virus-preloaded bags and plate respectively, and then cultured for 8 hours in an incubator at 37° C. and 5% $CO_2$ (a total number of cells of $1×10^7$ cells/PL30 bag). Next, the cells under each test condition were suspended and diluted 4-fold using an RPMI1640 medium containing 10% FBS and 1% penicillin-streptomycin, and then cultured for further 3 days.

(2) Analysis of Gene Transfer Efficiency

Using the cells obtained in Example 8-(1) that were equivalent to $1×10^6$ cells, the number of transferred vector copies was measured in the same manner as in Example 6-(3). Results are shown in Table 10 below.

TABLE 10

| Vessel | Incubation Time (hr) | Number of Transferred Vector Copies/Cell |
|---|---|---|
| PL30 | 12 | 1.82 |
| PL30 | 16 | 1.88 |
| PL30 | 24 | 2.64 |
| 24-Well Plate | 16 | 2.05 |

As a result, even when the PL30 bag was used, sufficient gene transfer efficiency was shown in all test conditions, and furthermore, when the incubation time was 24 hours, a gene transfer efficiency higher than that in the plate was shown.

Example 9

Study of Large Scale Bag Infection (1) Solution Mobility Test in Large Scale Bag Into a gas permeable culture bag PERMALIFE™ PL325 (culture area of 362.6 cm$^2$) (manufactured by OriGen Biomedical) was injected 180 mL of an RPMI1640 medium containing 10% FBS and 1% penicillin-streptomycin. The culture bag was subjected to horizontal reciprocating shaking at an inclination angle of 0° and 50 rpm or a seesaw-type shaking at an inclination angle of 4° and 35 rpm, while air was not injected into the bag. As a result, when the PL325 bag was used, sufficient mobility over the whole area of the bag was attained even without injecting air into the bag.

(2) Transfer of MazF Gene into SupT1 Cells

To a PL325 bag was added 65 mL/bag of 20 μg/mL CH-296. The bag was incubated overnight at 4° C., and then washed twice with 108 mL of PBS. The bag thus prepared (referred to as a CH-296-coated bag) was used in the following experiments.

The MT-MFRS retrovirus solution prepared in Example 6-(1) was diluted 4-fold with a GT-T-Retrol medium to prepare a diluted virus solution. To the CH-296-coated bag was added 180 mL of the diluted virus solution, and to each well of a CH-296-coated plate was added 1 mL of the diluted virus solution. For the PL325 bag, preloading was performed under two types of conditions: horizontal reciprocating shaking at an inclination angle of 0° and 50 rpm without injecting air, and seesaw-type shaking at an inclination angle of 4° and 35 rpm without injecting air. The plate was subjected to horizontal reciprocating shaking at an inclination angle of 0° and 100 rpm. In all cases, the incubation time was 16 hours. After the incubation, the virus solution was removed, and the bags and plate were washed respectively with 108 mL/bag and 0.5 mL/well of PBS containing 1.5% HSA. Subsequently, SupT1 cell suspension prepared so as to be 4×10$^5$ cells/mL using an RPMI1640 medium containing 10% FBS and 1% penicillin-streptomycin was injected in amounts of 180 mL/bag and 1 mL/well into the above-described virus-preloaded bags and plate respectively, and then cultured for 8 hours in an incubator at 37° C. and 5% $CO_2$ (a total number of cells of 7.2×10$^7$ cells/bag).

After 8 hours, for the plate test, the cells were diluted 4-fold with an RPMI1640 medium containing 10% FBS and 1% penicillin-streptomycin in a nontreated 24-well plate, and then cultured for further 3 days. For the PL325 bag test, 1.5 mL of the cultured cell was sampled, diluted 4-fold in a nontreated 24-well plate in the same manner as in the plate test, and then cultured for further 3 days. After sampling, the bag was turned upside down and then cultured in an incubator with 5% $CO_2$ for further 3 days to perform infection on the bag surface that was different from the surface infected until 8 hours.

(2) Analysis of Gene Transfer Efficiency

Using the cells obtained in Example 9-(1) that were equivalent to 1×10$^6$ cells, the number of transferred vector copies was measured in the same manner as in Example 6-(3). Results are shown in Table 11 below.

TABLE 11

| Vessel | Shaking | Inversion of Bag | Number of Transferred Vector Copies/Cell |
|---|---|---|---|
| PL325 Bag | Inclination Angle of 0° 50 rpm Horizontal reciprocating shaking | No | 2.29 |
| PL325 Bag | Inclination Angle of 4° 35 rpm Seesaw-Type shaking | No | 1.72 |
| PL325 Bag | Inclination Angle of 0° 50 rpm Horizontal reciprocating shaking | Yes | 3.15 |
| PL325 Bag | Inclination Angle of 4° 35 rpm Seesaw-Type shaking | Yes | 3.12 |
| 24-Well Plate | Inclination Angle of 0° 100 rpm Horizontal reciprocating shaking | | 2.05 |

As a result, even when the large scale bag PL325 was used, sufficient gene transfer efficiencies, which were equivalent to the gene transfer efficiency in the 24-well plate, were attained by preloading with horizontal reciprocating shaking or seesaw-type shaking. Furthermore, a gene transfer efficiency higher than that in the plate was shown when the bag was turned upside down during infection. Therefore, it was found that the gene transfer method of the present invention was greatly suitable for gene transfer into a large amount of cells using a large scale bag.

Example 10

Reuse Test of Virus Solution (1) Preloading 1 of Virus Solution (Recovery of Used Virus Solution)

To a PL325 bag was added 65 mL/bag of 20 μg/mL CH-296. The bag was incubated overnight at 4° C., and then washed twice with 100 mL of ACD-A. The bag thus prepared was referred to as a CH-296-coated bag.

To a CH-296-coated bag was added 180 mL of an undiluted MT-MFR3 retrovirus solution prepared in the same manner as in Example 6-(1). Preloading was performed under the conditions of horizontal reciprocating shaking at an inclination angle of 0° and 50 rpm without injecting air. The incubation temperature was 4° C., and the incubation time was 16 hours. After the incubation, the virus solution was recovered to obtain a used virus solution.

(2) Preloading 2 of Virus Solution

In order to investigate the transfer efficiency with the used virus solution, 1 mL of a virus solution was added to each well of a CH-296-coated plate prepared in the same manner as in Example 1-(2). As the virus solution, total of 4 types of virus solutions: an undiluted virus solution in the same lot-as the undiluted virus solution used in Example 10-(1) (New Virus), the used virus solution (Used Virus), New Virus diluted 2-fold with GT-T-Retrol (New Virus+GT-T-Retrol), and New Virus diluted with Used Virus (New Virus+Used Virus) were used. Thereafter, the plate was shaken at a shaking rate of 100 rpm at 4° C. for 16.5 hours, using a horizontal reciprocating shaker (MMS-3010: manufactured by TOKYO RIKAKIKAI CO, LTD.) at an inclination angle of 0° and a shaking width of 2.5 cm. After the incubation, the virus solution was removed, and the plate was washed with 0.5 mL/well of saline containing 1.5% HSA.

(3) Gene Transfer into Cell

Into the above-described virus-preloaded plate was injected 1 mL of SupT1 cell suspension prepared so as to be $5 \times 10^5$ cells/mL using an RPMI1640 medium containing 10% FBS and 1% penicillin-streptomycin, and then cultured for 24 hours in an incubator at 37° C. and 5% $CO_2$. Next, the cells in each test condition were suspended, diluted 5-fold using an RPMI1640 medium containing 10% FBS and 1% penicillin-streptomycin, and then cultured for further 2 days.

(4) Analysis of Gene Transfer Efficiency

Using the cells obtained in Example 10-(1) that were equivalent to $1 \times 10^6$ cells, the number of transferred vector copies was measured in the same manner as in Example 6-(3). The result is shown in Table 10 below.

TABLE 12

| Virus | Number of Transferred Vector Copies/Cell |
|---|---|
| Undiluted New Virus Solution | 3.80 |
| Undiluted Used Virus Solution | 2.26 |
| New Virus 2-Fold Diluted with GT-T-RetroI | 2.26 |
| New Virus 2-Fold Diluted with Used Virus | 2.81 |

As a result, the used virus solution recovered after preloading at 4° C. for 16.5 hours had the same titer as that of two-dilution of an unused virus solution. According to the present Example, it was demonstrated that the virus solution after used in virus preloading at a low temperature in the gene transfer method of the present invention was suitable for reuse.

Example 11

Study 1 of Incubation Time (Large Scale Bag Transduction)

(1) Transfer of MazF Gene into SupT1 Cells

An MT-MFR3 retrovirus solution prepared in the same manner as in Example 6-(1) was diluted 4-fold with a GT-T-RetroI medium to prepare a diluted virus solution. The diluted virus solution was added in amounts of 180 mL/bag and 0.5 mL/well to a CH-296-coated bag prepared using a gas permeable culture bag PERMALIFE™ PL325 (manufactured by OriGen Biomedical) in the same manner as in Example 9-(2) and a CH-296-coated plate, respectively. For the PL325 bag, preloading was performed with horizontal reciprocating shaking at an inclination angle of 0° and 50 rpm without injecting air. The plate was subjected to horizontal reciprocating shaking at an inclination angle of 0° and 100 rpm. The incubation time was 16, 24, or 48 hours for the PL325 bag, and 16 hours for the plate. After the incubation, the virus solution was removed, and the bags and plate were respectively washed with 108 mL/bag and 0.5 mL/well of PBS containing 1.5% HSA. Subsequently, SupT1 cell suspension prepared so as to be $5 \times 10^5$ cells/mL using an RPMI1640 medium containing 10% FBS and 1% penicillin-streptomycin was injected in amounts of 180 mL/bag and 1 mL/plate into the above-described virus-preloaded bag and plate respectively, and then cultured in an incubator at 37° C. and 5% $CO_2$ (a total number of cells of $7.2 \times 10^7$ cells/bag). After 8 hours, for the bag test, the bag was turned upside down, and then cultured in an incubator at 37° C. and 5% $CO_2$.

The next day, for the plate test, the cells were diluted 5-fold with an RPMI1640 medium containing 10% FBS and 1% penicillin-streptomycin in a nontreated 24-well plate, and then cultured for further 2 days. For the PL325 bag test, 1.5 mL of the cultured cell was sampled, diluted 5-fold in a nontreated 24-well plate in the same manner as in the plate test, and then cultured for further 2 days.

(2) Analysis of Gene Transfer Efficiency

Using the cells obtained in Example 11-(1) that were equivalent to $1 \times 10^6$ cells, the number of transferred vector copies was measured in the same manner as in Example 6-(3). Results are shown in Table 13 below.

TABLE 13

| Vessel | Incubation Time | Number of Transferred Vector Copies/Cell |
|---|---|---|
| PL325 Bag | 16 hours | 2.50 |
| PL325 Bag | 24 hours | 2.04 |
| PL325 Bag | 48 hours | 1.74 |
| 24-Well Plate | 16 hours | 1.48 |

As a result, when the large scale bag PL325 was used, a higher gene transfer efficiency was shown in all test conditions as compared with the plate test. Furthermore, an incubation time of 16 hours was the most effective in the present Example.

Example 12

Study 2 of Incubation Time (Large Scale Bag Transduction)

(1) Transfer of MazF Gene into SupT1 Cells

An MT-MFR3 retrovirus solution prepared in the same manner as in Example 6-(1) was diluted 4-fold with a GT-T-RetroI medium to prepare a diluted virus solution. The diluted solution was added in amounts of 180 mL/bag and 0.5 mL/well to a CH-296-coated bag prepared in the same manner as in Example 9-(2) using a gas permeable culture bag PERMALIFE™ PL325 (manufactured by OriGen Biomedical) and a CH-296-coated plate, respectively. For the PL325 bag, preloading was performed with horizontal reciprocating shaking at an inclination angle of 0° and 50 rpm without injecting air. The plate was subjected to horizontal reciprocating shaking at an inclination angle of 0° and 100 rpm. The incubation time was 8, 12, 16, or 20 hours for the PL325, and 16 hours for the plate. After the incubation, the virus solution was removed, and the bags and plate were washed respectively with 108 mL/bag and 0.5 mL/well of PBS containing 1.5% HSA. Subsequently, SupT1 cell suspension prepared so as to be $5 \times 10^5$ cells/mL using an RPMI1640 medium containing 10% FBS and 1% penicillin-streptomycin was injected in amounts of 180 mL/bag and 1 mL/plate into the above-described virus-preloaded bags and plate respectively, and then cultured in an incubator at 37° C. and 5% $CO_2$ (a total number of cells of $7.2 \times 10^7$ cells/bag). After 2 hours, for the bag test, the bag was turned upside down, and then cultured in an incubator at 37° C. and 5% $CO_2$.

The next day, for the plate test, the cells were diluted 5-fold with an RPMI1640 medium containing 10% FBS and 1% penicillin-streptomycin in a nontreated 24-well plate, and then cultured for further 3 days. For the PL325 bag test, 1.5 mL of the cultured cell was sampled, and diluted 5-fold in a nontreated 24-well plate in the same manner as in the plate test, and then cultured for further 3 days.

(2) Analysis of Gene Transfer Efficiency

Using the cells obtained in Example 12-(1) that were equivalent to $1 \times 10^6$ cells, the number of transferred vector copies was measured in the same manner as in Example 6-(3). Results are shown in Table 14 below.

TABLE 14

| Vessel | Incubation Time | Number of Transferred Vector Copies/Cell |
|---|---|---|
| PL325 Bag | 8 hours | 1.93 |
| PL325 Bag | 12 hours | 2.64 |
| PL325 Bag | 16 hours | 2.34 |
| PL325 Bag | 20 hours | 1.89 |
| 24-Well Plate | 16 hours | 1.70 |

As a result, when the large scale bag PL325 was used, a higher gene transfer efficiency was shown in all test conditions as compared with the plate test. Furthermore, incubation times of 12 hours and 16 hours were the most effective in the present Example.

INDUSTRIAL APPLICABILITY

According to the present invention, a convenient and highly efficient gene transfer method is provided. The present invention is specifically useful in the fields of medicine, cell technology, genetic technology, developmental technology and the like.

The invention claimed is:

1. A method of transferring a foreign gene into a target cell using a retroviral vector, the method comprising the following steps (a) to (e):
   (a) immobilizing a retrovirus-binding substance on an inner surface of a bag for cell culture;
   (b) injecting a liquid containing a retroviral vector carrying a foreign gene into the bag obtained by the step (a), followed by incubation with shaking at a temperature of less than 25° C. for 8 hours to 48 hours to obtain a bag to which the retroviral vector is bound;
   (c) adding a target cell into the bag obtained by the step (b), followed by incubation for 2 to 8 hours;
   (d) turning the bag obtained by the step (c) upside down; and then
   (e) incubating the bag obtained by the step (d) while upside down.

2. The method for transferring a gene according to claim 1, further comprising a step of washing the bag obtained by the step (b) prior to the step (c).

3. The method according to claim 1, wherein the retrovirus-binding substance is at least one selected from the group consisting of fibronectin, fibroblast growth factor, collagen type V, polylysine, DEAE-dextran, CH-296, H-271, H-296, and CH-271.

4. The method according to claim 1, wherein the retrovirus-binding substance also has a cell-binding activity.

5. The method according to claim 1, wherein the step (a) further comprises immobilizing a cell-binding substance on the inner surface of the bag.

6. The method according to claim 5, wherein the cell-binding substance is at least one selected from the group consisting of a cell-adhesive protein, a hormone, a cytokine, an antibody, a sugar chain, and a carbohydrate.

* * * * *